United States Patent [19]

Albers

[11] 4,008,689
[45] Feb. 22, 1977

[54] WASTE COLLECTION AND CONVERSION SYSTEM

[76] Inventor: Teo Albers, 18007 Arline Ave., Artesia, Calif. 90701

[22] Filed: July 25, 1975

[21] Appl. No.: 591,776

[52] U.S. Cl. .................................................. 119/28
[51] Int. Cl.² ............................................. A01K 1/00
[58] Field of Search ....................... 119/28, 15, 16

[56] References Cited

UNITED STATES PATENTS

| 250,631 | 12/1881 | Fisher et al. | 119/28 |
| 3,137,270 | 6/1964 | Rigterink et al. | 119/28 X |
| 3,213,828 | 10/1965 | Sorensen | 119/28 X |
| 3,223,070 | 12/1965 | Gribble et al. | 119/16 |
| 3,918,404 | 11/1975 | Bunger | 119/28 |

Primary Examiner—Hugh R. Chamblee

[57] ABSTRACT

A passive waste collection system including a trough disposed to collect animal waste having an adjustable end baffle for controlling the depth of the accumulated waste therein. Any fermented waste spills over the baffle onto a spring-biased valve and when the waste load on the valve exceeds the spring bias, the valve opens to permit the transfer of the waste to a fermentation tank. The ullage of the fermentation tank in turn communicates with an accumulator to collect the fermentation gases for use in the production of energy.

3 Claims, 1 Drawing Figure

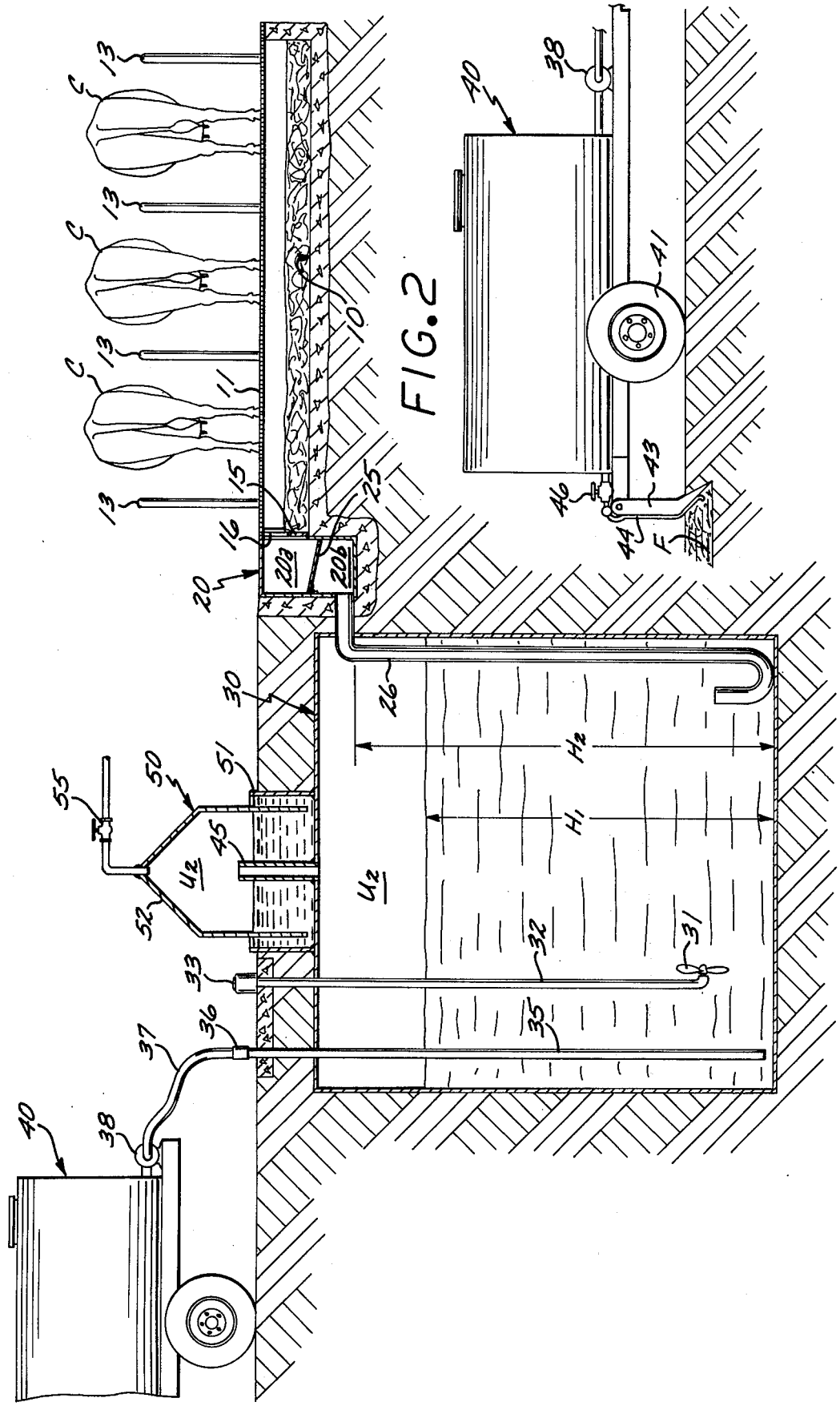

WASTE COLLECTION AND CONVERSION SYSTEM

BACKGROUND OF THE INVENTION

1. Field of the Invention

The present invention relates to waste treatment systems and more particularly to waste conversion facilities where animal waste such as the waste produced by cattle is converted to methane gas and to fertilizer.

2. Description of the Prior Art

In present day farming operations the production of waste by the large numbers of cattle usually involved presents a formidable disposal problem and many various techniques for removing such animal waste to some remote collection area have been developed in the past. Most such techniques operate either on the basis of a conveyor belt, with the cattle aligned over the conveyor belt to deposit their waste thereon, or on the basis of periodic scraping where the waste built up in some collection area, such as a trough immediately behind the animals, is removed periodically.

Accordingly, most prior art techniques take benefit of heavy power equipment to accomplish the purpose described herein. In present power shortages this involvement of heavy equipment in waste removal presents a large cost to the farmer, increasing the cost of food production without providing a convenient means of recovering the power available in animal waste.

SUMMARY OF THE INVENTION

Accordingly, it is the general purpose and object of the present invention to provide a passive waste-feed arrangement which directly conveys the animal waste to a fermentation facility and which thus takes benefit of the digestive fluids residual in the waste to promote the conveying propagation of the waste.

Other objects of the invention are to provide a passive waste delivery system which can be conveniently adjusted to accommodate any number of waste producing cattle, and which furthermore can be conveniently adjusted to accommodate various environments and seasons.

Yet further objects of the invention are to provide a waste delivery system which is easy to produce, simple to maintain and requires few parts.

These and other objects are accomplished within the present invention by forming a trough in the rear section of a plurality of cattle-receiving stanchions, such trough being covered by a grate to support the hind quarters of the cattle thereon and to permit passage of the waste dropped by the cattle into the trough. The trough is permanently closed at one end, the other end closure thereof being formed by an adjustable baffle whereby the height of the waste or debris accumulated in the trough can be conveniently adjusted. Once the debris or waste exceeds the height set by this baffle, the liquid constituents thereof spill over the upper edge of the baffle into a trap to deposit on top of a spring loaded valve separating the trap into an upper and lower chamber. When the weight of the accumulated liquid debris on top of the valve exceeds the spring bias thereof, the valve will drop downwardly to pass the waste so collected into the lower chamber thereof. This waste or debris so collected in the lower chamber of the trap is then communicated to a fermentation tank by a transfer pipe having an inlet opening disposed proximate the bottom surface of the trap and the exit opening adjacent the bottom of the fermentation tank. In order to accommodate the ullage pressures developed within the fermentation tank and to provide a liquid seal to contain such pressures, the inlet opening of the transfer pipe, or the bottom surface of the trap, is arranged at a level substantially above the liquid level within the fermentation tank. Thus the ullage pressure within the fermentation tank must exceed the water column height in the transfer pipe in order to allow any backflow of the gas produced into the interior of the trap. Should such gases be inadvertently released into the trap, the inclusion of the spring valve covered with the debris on the top thereof provides a redundant seal, thus preventing any possibility of gas leakage which could potentially become a hazard. The gases produced in the ullage of the fermentation tank as the by-product of fermentation are conveyed through an upwardly extending ullage vent into the ullage of an expandable gas container formed in the manner of a telescoping dome having the opening thereof immersed in a liquid seal. The by-product gases are thus accumulated in the gas container to be available for use as an energy source for whatever applications necessary in farm production. As is conventional in the art, the fermentation tank is provided with an agitator and a stand pipe useful for withdrawing the accumulated debris therefrom which is then collected in a mobile tank such as a waste dispensing plough to be used as fertilizer.

BRIEF DESCRIPTION OF THE DRAWINGS

FIG. 1 is a diagrammatic illustration in partial cross section of the inventive system disclosed herein; and FIG. 2 is a side view illustration of a waste dispensing plough useful with the present invention.

DESCRIPTION OF THE SPECIFIC EMBODIMENT

As shown in FIG. 1, the present invention includes a trough generally designated by the numeral 10 covered by a grating 11, trough 10 being formed in the floor of the barn in alignment below the hind quarters of cattle C as they are aligned in their feeding position within stanchions 13. As illustrated herein, trough 10 is closed at one end and includes at the other end a sliding baffle 15 receivable within a vertically disposed peripheral groove 16 for vertical articulation. In this manner, the depth of the debris collected within trough 10 can be conveniently adjusted by selective vertical alignment of baffle 15, the upper edge of baffle 15 thus defining the depth of the accumulated waste above the bottom surface of the trough. On the distal side of baffle 15 trough 10 drains into a trap 20 formed in the floor of the barn to extend below the bottom surface of trough 10. Trap 20 includes a spring-loaded valve 25 disposed horizontally thereacross at a vertical station below the bottom surface once more of trough 10, valve 25 thus dividing the trap 20 into an upper chamber 20a and a lower chamber 20b.

Thus, as the cattle C are feeding within the stanchions 13, their concurrent and subsequent production of waste is deposited directly through the grating 11 into the trough 10. This waste is comingled with various bacteria including the digestive bacteria of the animals to promote further decomposition within the trough. Depending on the temperature, humidity and number of cattle standing over the trough, the adjustment of baffle 15 provides for convenient control over the depth of the waste or debris accumulated and therefore a convenient control over the decomposition process therein. As the waste is continuously deposited into this trough, this decomposition process reduces most of the waste into liquid form until the liquid accumulated in the trough exceeds the height of baffle 15. Once exceeded, the liquid will spill over the baffle 15 to deposit on the top of the spring-loaded valve 25 until the spring bias of the valve is exceeded by the weight thereof.

Referring back to FIG. 1, the lower chamber 20$b$ of the trap 20 is arranged at a level substantially above the liquid level within an underground fermentation tank 30. A communicating path between the lower chamber 20$b$ and tank 30 is established by way of a transfer pipe 26 which communicates from the bottom of trap 20 into the interior of the fermentation tank 30 and extends downwardly therein to terminate proximate the bottom of the tank.

Within the fermentation tank 30 the continued collection of waste products eventually reaches a level shown herein as level $H_1$. The entry opening of pipe 26 is disposed at a substantially higher vertical station shown herein as level $H_2$. The vertical differential between levels $H_1$ and $H_2$ provides for a liquid seal within pipe 26 which isolates the gas pressures produced within the ullage $U_1$ of tank 30 from the interior of chamber 20$b$. Should the pressure head in tank 30 exceed the liquid column in pipe 26, the further provision of the spring-loaded valve 25 in combination with the liquid seepage across baffle 15 continuously deposited on the upper surface thereof provides a redundant seal, sealing off chamber 20$b$.

As is conventional in the art, the fermentation tank 30 is provided with an agitator illustrated by way of a propeller 31 at the lower end of a downwardly-extending pipe 32 which at its upper end communicates across the upper wall of tank 30 to an electrical motor 33. In addition to the agitator there is a withdrawal standpipe 35 having a lower opening proximate the bottom of tank 30 and again extending across the top surface thereof to terminate in a connection fitting 36 adapted to connect to a flexible hose 37. Hose 37, at the other end, connects to the inlet side of a pump 38 mounted to feed the evacuated waste or the debris into the interior of a mobile tank 40.

Thus, by way of the natural process of fermentation within tank 30, the gases within the ullage $U_1$ accumulate a gas mixture containing methane and various other hydrocarbons suitable as an energy source. These gases are conveyed upwardly through an ullage vent 45 extending through the upper surface of tank 30 into the interior of a variable volume gas container shown generally as container 50. The ullage vent 45 is formed generally as a vertical pipe extending from the lid or the upper surface of tank 30 into the ullage of container 50, designated herein as ullage $U_2$.

The gas container 50 is conventionally arranged to provide a variable volume by a combination of a liquid-filled ring 51 disposed horizontally on the exterior upper surface of tank 30 into which the opening of an inverted dome 52 is telescopically immersed. By controlling the weight of the dome 52 and the surface area thereof, a controlled ullage pressure within ullage $U_2$, and therefore within ullage $U_1$, can be developed. Thus the gas container 50 acts as an accumulator maintaining substantially constant pressure within both ullages which by proper selection of weight and surface area of the dome 52 can be set not to exceed the pressure head accommodated by the vertical height of the inlet pipe 26. The gases so accumulated within the gas container 50 are then withdrawn for any desired use by way of a control valve 55 connected in series with the ullage $U_2$.

As an adjunct to the inventive process and apparatus described herein, the mobile container 40 is mounted on wheels 41 and includes on one end thereof distal to pump 38, a hinged plough 43. Disposed over the back surface of plough 43 is a flexible dispensing tube 44 which, across a valve 46, communicates with the interior of the mobile tank 40. Thus, the waste collected and sedimented during the process of fermentation is deposited within a furrow F formed by drawing plough 43 through the ground, providing a convenient technique of dispensing this waste as fertilizer during the turning of the ground.

Some of the many advantages of the present invention should now be readily apparent. The invention provides, by way of simple and expedient devices, apparatus which avoids many of the power-consuming tasks typically involved in an animal farm while at the same time providing gases useful for heating or with other power uses as a by-product of such collection. This the invention does with apparatus which is simple to produce and easy to maintain.

Obviously, many modifications and variations of the present invention will be apparent to those skilled in the art. It is therefore intended that the scope of the invention be solely limited by the claims appended hereto.

What is claimed is:

1. A waste collection system adapted to collect animal waste for fermentation, comprising:
 a trough formed in the ground surface of an animal-retaining enclosure closed at one end and including a vertically adjustable baffle at the other end;
 a spring-loaded flapper valve disposed on the distal side of said baffle closing a cavity arranged below the bottom surface of said trough;
 a fermentation tank disposed below said cavity;
 transfer means connecting said tank to said cavity;
 gas-accumulating means disposed above said tank for collecting the ullage gases therefrom; and
 said accumulating means includes a liquid-filled ring disposed on the upper surface of said tank, an inverted dome having the opening thereof immersed in said liquid-filled ring and a vent connecting the ullage in said tank with the ullage in said dome.

2. Apparatus according to claim 1 wherein:
 said tank is disposed below said cavity at a vertical displacement corresponding to a water column greater than the pressure developed by said dome.

3. Apparatus according to claim 2 wherein:
 said tank includes agitation means on the interior thereof for agitating any fluids therein and withdrawal means connected to the exterior of said tank for withdrawing said fluids from the interior thereof.

* * * * *